United States Patent
St. Onge et al.

(10) Patent No.: US 10,292,693 B2
(45) Date of Patent: May 21, 2019

(54) DEVICES FOR INTRODUCING MULTIPLE INSTRUMENTS AND METHODS OF USE

(71) Applicant: Boston Scientific Scimed, Inc., Maple Grove, MN (US)

(72) Inventors: Andre D. St. Onge, Waltham, MA (US); Naroun Suon, Lawrence, MA (US); Barry Weitzner, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 183 days.

(21) Appl. No.: 15/406,278

(22) Filed: Jan. 13, 2017

(65) Prior Publication Data

US 2017/0128060 A1    May 11, 2017

Related U.S. Application Data (63) Continuation of application No. 14/486,006, filed on Sep. 15, 2014, now Pat. No. 9,579,093, which is a continuation of application No. 12/898,965, filed on Oct. 6, 2010, now Pat. No. 8,864,653.

(60) Provisional application No. 61/249,317, filed on Oct. 7, 2009.

(51) Int. Cl.

| | |
|---|---|
| *A61B 1/00* | (2006.01) |
| *A61B 17/02* | (2006.01) |
| *A61B 1/018* | (2006.01) |
| *A61B 17/34* | (2006.01) |

(52) U.S. Cl.
CPC ........ *A61B 17/0218* (2013.01); *A61B 1/0008* (2013.01); *A61B 1/00098* (2013.01); *A61B 1/00101* (2013.01); *A61B 1/018* (2013.01); *A61B 17/3421* (2013.01); *A61B 2017/3445* (2013.01); *A61B 2017/3449* (2013.01)

(58) Field of Classification Search
CPC .............. A61B 1/0008; A61B 1/00098; A61B 1/00101; A61B 1/018; A61B 17/0218; A61B 17/3421; A61B 2017/3445; A61B 2017/3449
See application file for complete search history.

(56) References Cited

U.S. PATENT DOCUMENTS

| | | |
|---|---|---|
| 3,631,848 A | 1/1972 | Muller |
| 5,460,168 A | 10/1995 | Masabuchi et al. |
| 5,976,073 A | 11/1999 | Ouchi |
| 5,976,077 A | 11/1999 | Wittens et al. |
| 6,352,503 B1 | 3/2002 | Matsui et al. |
| 2005/0090709 A1 | 4/2005 | Okada et al. |
| 2007/0191767 A1 | 8/2007 | Hennessy et al. |
| 2007/0282166 A1 | 12/2007 | Ayala et al. |
| 2008/0188869 A1 | 8/2008 | Weitzner et al. |
| 2008/0243176 A1 | 10/2008 | Weitzner et al. |
| 2008/0287961 A1 | 11/2008 | Miyamoto et al. |

OTHER PUBLICATIONS

International Search Report and Written Opinion in International Application No. PCT/US2010/051604, dated Jan. 18, 2011.

*Primary Examiner* — Timothy J Neal
(74) *Attorney, Agent, or Firm* — Bookoff McAndrews, PLLC (57) ABSTRACT

Disclosed herein are devices and methods for introducing a plurality of instruments to a target site through a working channel. The working channel can include a surface adapted to guide one or more instruments into select positions. The working channel can be defined by a portion of a guide tube or tip that may be coupled with an endoscope.

20 Claims, 9 Drawing Sheets

DEVICES FOR INTRODUCING MULTIPLE INSTRUMENTS AND METHODS OF USE

This application is a continuation of U.S. application Ser. No. 14/486,006, filed Sep. 15, 2014, which is a continuation of U.S. application Ser. No. 12/898,965, filed Oct. 6, 2010, now U.S. Pat. No. 8,864,653, issued Oct. 21, 2014, which claims the benefit of priority from U.S. Provisional Application No. 61/249,317, filed Oct. 7, 2009. Each of the above-referenced applications is herein incorporated by reference in its entirety.

FIELD OF THE INVENTION

Embodiments of the present invention relate to devices used for endoscopic surgery. In particular, exemplary embodiments of the present invention relate to devices for introducing multiple instruments to a surgical site. Embodiments of the present invention also cover methods of using such devices.

BACKGROUND OF THE INVENTION

Endoscopic surgery usually involves accessing a surgical site through a small incision in the patient's body or a natural body orifice. One goal of endoscopic surgery is to reduce tissue trauma and the body's response to injuries associated with traditional "open" surgery. Examples of some common endoscopic procedures include laparoscopic cholecystectomies (i.e., gall bladder removal) and appendectomies; arthroscopic surgery of the interior of bone joints; endoscopic rhinosinusitis; colonoscopic excisions; endoscopic discectomy; etc. In addition to medical applications, endoscopic systems may be used for visualization and manipulation of complex technical systems, improvised explosive devices, architectural scale models, and other non-medical applications.

Conventional endoscopes are often configured to deliver optical devices and surgical instruments to a surgical site. Such optical devices usually include two fiber optic lines for imaging the site. A "light fiber" carries light to the site, while an "image fiber" carries an image of the site back to the endoscope's operator.

Conventional endoscopes typically include a working channel for introducing surgical instruments to a target surgical site. These instruments can have end-effectors, such as forceps, scissors, brushes, etc. for tissue excision, sampling, or other diagnostic and surgical work. Some endoscopes can also include a separate axial port or channel for administration of drugs, suction, or irrigation.

The growing capabilities of endoscopes have allowed operators to perform an increasing variety of surgeries and diagnostic and/or therapeutic procedures. Further refinement of endoscopic devices may enable operators to less invasively perform complicated procedures, thereby reducing post-operative pain, scar tissue formation, or recovery time. Reducing the size of endoscopic equipment also would allow greater access to target sites within body regions that are currently difficult to treat with conventional endoscopic systems.

Conventionally multiple instruments for endoscopic procedures are delivered to the target site through separate working channels of a single endoscope. These separate working channels running the full length of the endoscope maintain the positions of the instruments relative to one another, relative to optics, and relative to the body of the endoscope. For example, a grasper inserted through a left-side channel of a conventional endoscope will be located to the left of a grasper inserted through a separate right-side channel throughout the length of the endoscope.

Conventional endoscopes having two or more working channels can be large and unsuitable for some endoscopic procedures. The elimination of separate working channels within at least part of an endoscope could reduce the diameter of at least part of the endoscope. Additionally, the ability to deliver multiple instruments through a single lumen increases the number of instruments available at the surgical site. Delivering multiple instruments simultaneously may facilitate more complex endoscopic surgeries.

The present disclosure describes devices and methods for delivering multiple instruments to a surgical site.

SUMMARY OF THE INVENTION

Described herein are various devices for introducing a plurality of instruments to a target site through a single channel of an elongate body. For example, embodiments of the current disclosure provide a device having a single proximal lumen that can divide into multiple distal lumens. Such a design can lower a radial dimension of the device by removing the need for individual channels to carry individual instruments.

In one aspect, the system may comprise an elongate guide tube or distally mounted working channel tip having at least one working channel through which multiple instruments may be delivered to the target site. The tip or guide tube can include a lumen configured to direct a first instrument into a first select position, and then permit a second instrument to be directed to a second select position. Thus, a portion of the tip or guide tube can provide an instrument directing surface such that an instrument delivered through the tip or guide tube can be positioned in a location relative to the body of the tip or guide tube, or relative to another instrument delivered through the tip or guide tube.

In one aspect, the working channel of a tip or guide tube can be configured to receive two instruments. The instrument directing surface can operate to directionally bias a first instrument, such as, for example, deflecting the first instrument toward a right hand side of the tip or guide tube. The first instrument or the instrument directing surface then affects the movement of a second instrument delivered through the working channel to assume a left-handed position.

The instrument directing surface can be positioned on or in a working channel of the tip or the guide tube. In one aspect, the tip can be integrally formed with the guide tube. In another aspect, the tip can be detachably coupled to the guide tube. The detachable tip can be disposable or can mate with an off-the-shelf endoscope to allow the use of multiple tools in a single conventional endoscope working channel.

Further described herein are methods of introducing a plurality of endoscopic instruments to a target site. In one embodiment, a guide tube having at least one working channel and a distal working channel tip may be directed to a target site. At least two surgical instruments then may be delivered through the working channel and the distal tip, wherein the shape and size of an inner surface of the tip directs the instruments into select positions within the tip.

In yet another aspect, the tip or guide tube includes multiple distal working channels that branch from a single proximal working channel. One or more instrument directing surfaces can direct multiple instruments, inserted into the proximal working channel sequentially, into select distal working channel branches. For example, an endoscope may be directed to a centrally-located distal working branch. Two subsequently inserted instruments may then be directed to generally left-side and right-side, or off-center, distal working channel branches.

The applications of the disclosed systems and methods include, but are not limited to, trans-oral, trans-anal, trans-vaginal, trans-nasal, laparoscopic, arthroscopic, thoracoscopic, and panendoscopic surgeries. In addition, while the described systems and methods may generally refer to "surgical instruments" for convenience, they are not limited to surgical, or other therapeutic, interventions. In particular, the described systems and methods may be used for various diagnostic applications, such as collection of tissue biopsy samples, gastroscopy for visualization of ulcers within the upper GI tract, hysteroscopy for diagnosis of intrauterine pathology, etc. In addition, the systems and methods described herein can be used for non-medical applications, such as the inspection or repair of machinery.

It is to be understood that both the foregoing general description and the following detailed description are exemplary and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the disclosed system, devices and methods.

DESCRIPTION OF THE EMBODIMENTS

Reference will now be made to exemplary embodiments of the invention, examples of which are illustrated in the accompanying drawings. Wherever possible, the same reference numbers will be used throughout the drawings to refer to the same or like parts.

Figure 1:
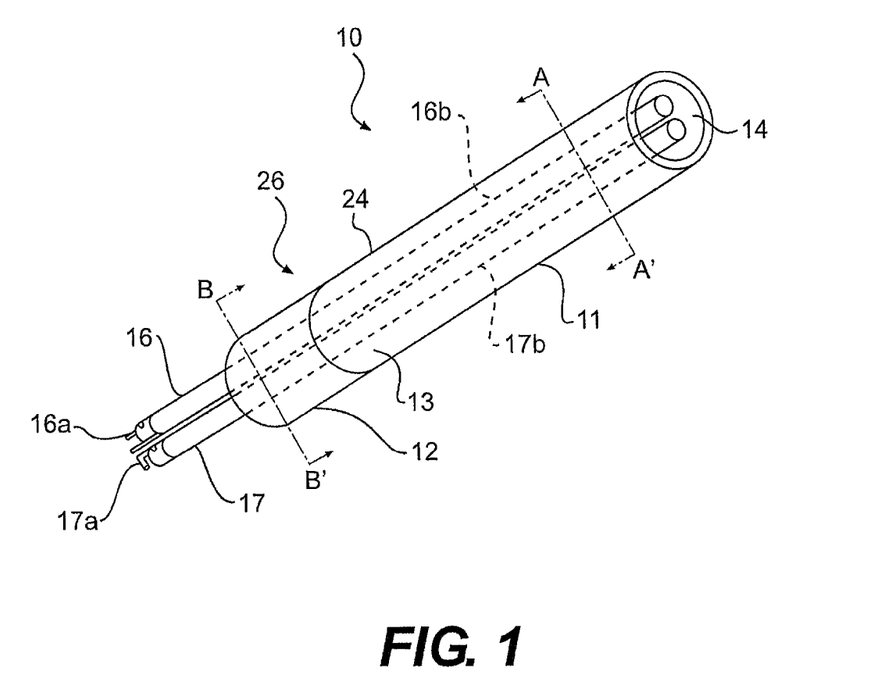
FIG. 1 is a perspective view of an exemplary embodiment of a system described herein.

FIG. 1 illustrates a perspective view of a system 10 for performing a surgical, therapeutic, or diagnostic procedure. System 10 can include a guide tube 11 and a tip 12 for delivering one or more instruments to a target site. For example, as shown in FIG. 1, a first instrument 16 and a second instrument 17 are shown within system 10.

Instruments 16 and 17 can each include a proximally-located handle (not illustrated) for controlling distal articulation or operation of end-effectors 16a and 17a. The handles and the end-effectors 16a, 17a can be connected by rigid or flexible catheters 16b and 17b, respectively. The instruments can be disposed within system 10 such that end-effectors 16a and 17a can pass through system 10 and extend beyond a distal end of system 10 to a target site (not shown).

During a procedure, system 10 can be inserted into a patient through an opening and positioned near the target site. Instruments 16 and 17 can then be inserted into system 10 through one or more lumens or channels. As discussed below, system 10 can include one or more channels for the passage of instruments, optics, therapeutic substances, implants, or other therapeutic or diagnostic devices.

System 10 can be configured for insertion through a small incision or natural body lumen such as the colonic lumen or other gastrointestinal lumen. In one embodiment, system 10 is flexible and non-articulating. In another embodiment, at least a portion of system 10 includes an articulation section. For example, a segment 13 can provide one, two, or more than two degrees of freedom of movement to system 10. Articulation can be controlled via proximal user controls, as described in U.S. patent application Ser. No. 11/946,812, which is incorporated herein by reference. In addition, while system 10 is described as flexible, all or a portion of system 10 can be rigid.

Guide tube 11 can include a generally elongate body 24 extending between a proximal end (not illustrated) and a distal end 26. Guide tube 11 can also include one or more lumens or channels extending from a generally proximal region of guide tube 11 to a generally distal region of guide tube 11.

Figure 2A:
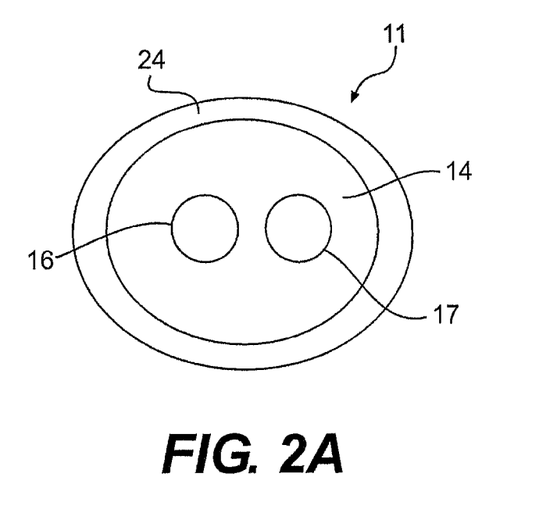
FIG. 2A is a cross-sectional view of FIG. 1 taken along line A-A'.

As shown in FIG. 2A (taken along line A-A' in FIG. 1), guide tube 11 can comprise a single channel configured to receive one or more instruments. For example, the outer walls of guide tube 11 can define a working channel 14 configured to receive instruments 16, 17.

Figure 2B:
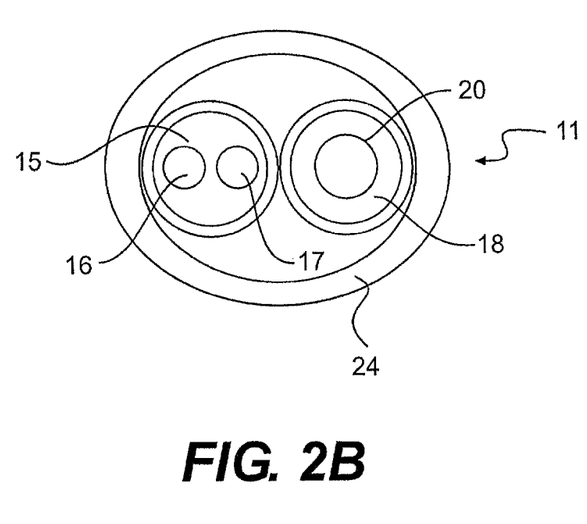
FIG. 2B is a cross-sectional view of another embodiment of a system.

In another embodiment, as illustrated in FIG. 2B, guide tube 11 can include multiple channels. For example, an optical channel 18 can be configured to receive an optical device 20, and a working channel 15 can be adapted to receive instruments 16, 17. As shown in FIG. 2B, working channel 15 can have a generally circular cross-section, however other suitable cross-sectional shapes may be used.

Figure 3:
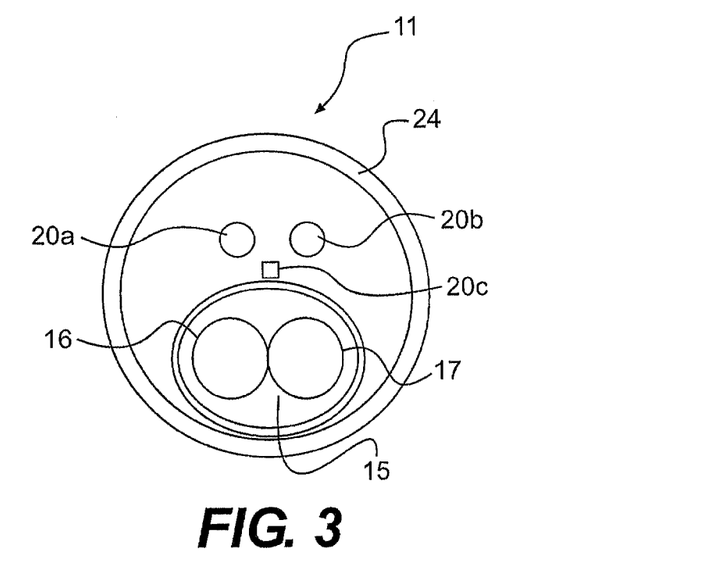
FIG. 3 is a cross-sectional view of another embodiment of a system.

In another embodiment, optical device 20 can be integrated within the structure of guide tube 11. Such an embodiment, as depicted in FIG. 3, can include an optical device 20a, a light source 20b, and a lens washer 20c. Various other embodiments of guide tube 11 having arrangements of components are known to one of skill in the art.

Figure 4:
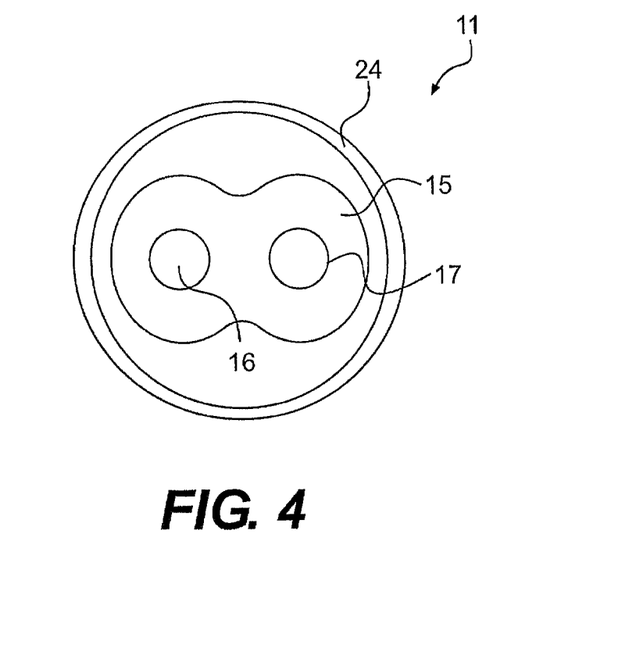
FIG. 4 is a cross-sectional view of another embodiment of a system.

In another exemplary embodiment illustrated in FIG. 4, working channel 15 can have a generally "dumbbell" shaped cross-section to facilitate the alignment and positioning of instruments 16, 17. The cross-section of the working channel lumen need not be limited to circular or dumbbell shapes, but can include any shape or configuration that would facilitate the insertion and alignment of instruments within a channel.

As shown in FIG. 1, system 10 can include tip 12 located generally distally along system 10. Tip 12 can function to direct the movement of one or more instruments into one or more select, desired positions as the instruments exit the distal end of system 10. In effect, tip 12 can operate to generally organize the relative locations of a plurality of instruments.

In an exemplary embodiment, tip 12 can be defined by a portion of guide tube 11, e.g. tip 12 can be integrally formed with tube 11. In another embodiment, working channel tip 12 can be permanently or detachably mated to a distal region of guide tube 11. As shown in FIG. 1, tip 12 can include a generally tubular structure and can be mated to distal end 26 of guide tube 11. These and other embodiments permit tip 12 to preferentially orient instruments as they exit system 10. For example, a tip 12 may be selected from a set of tips having different structures that result in different orientations/positions of the instruments relative to each other.

Tip 12 can be formed of any suitable material. Such materials can include a metal, polymer, or biocompatible material. Tip 12 can also be formed of a transparent or translucent material to permit visualization through tip 12.

Tip 12 can be adhered or mechanically coupled to guide tube 11. In one such embodiment, guide tube 11 and tip 12 can have complementary threads for connecting to each other. In yet another embodiment, tip 12 can be configured to mate via a snap fit. Other forms of attachment can include adhesives or mechanical connectors. Adhesives can include UV cure epoxy, heat cure epoxy, cyanoacrylates, or tape. Mechanical connectors can include crimping, swaging, ultrasonic welding, metal welding or soldering, or a bayonet mount.

In one embodiment, tip 12 can mate with a conventional endoscope or an off-the-shelf guide tube. For example, the proximal end of tip 12 can include a mating feature for detachably mating with the distal end of a conventional endoscope. In one such embodiment, a portion of tip 12 can be cinched or strapped around a portion of the endoscope.

Various devices, systems and methods may be used to removably connect or disconnect tip 12 to guide tube 11, an endoscope, or a similar device. For example, a sleeve (not shown) can extend over a portion of guide tube 11 and tip 12 to mate the two devices. In addition, tip 12 may be attached to a full length sleeve (not shown) that an endoscope or tool is inserted into.

Figure 5A:
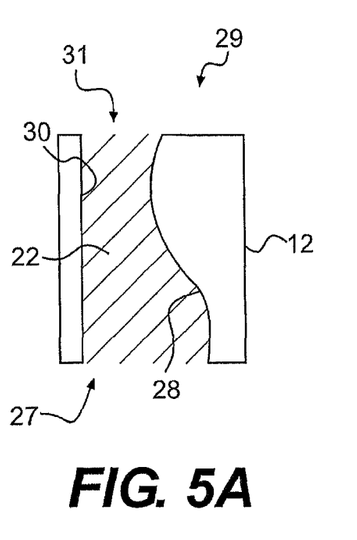
FIG. 5A is a longitudinal sectional view of the distal end of an exemplary embodiment.

As shown in FIG. 5A, tip 12 can include a proximal end 27 and a distal end 29. Tip 12 can also include one or more channels or integrated devices, such as, for example, an integrated optics device. For example, an optical channel in tip 12 can be aligned with an optical channel in guide tube 11 to permit ready passage of an optical device through guide tube 11 and tip 12.

Tip 12 can include one or more working channels which correspond to one or more working channels of guide tube body 24. In one aspect, tip 12 can include a single working channel 31. In another aspect, the working channel can branch from a proximally-located single working channel to two or more distally-located openings. In yet another aspect, tip 12 can include multiple working channels.

In one embodiment, tip 12 can include an inner surface 22, which can direct one or more instruments into one or more select, desired positions. As such, surface 22 may selectively position a plurality of instruments. In one aspect, surface 22 directs a first instrument into a first select position. Subsequent placement of a second instrument into tip 12 can result in the second instrument being directed to a second select position. The first and second positions can correspond to first and second areas within a single working channel. Alternatively, the first and second positions can refer to separate working channel branches or separate apertures.

In one aspect, inner surface 22 can include a funnel-like shape proximate to distal end 29 of tip 12. Other generally arcuate or linear shaped surfaces may similarly be configured to direct one or more instruments.

FIG. 5A illustrates a longitudinal cross-section of the distal end of tip 12 with surface 22 defined by a portion of channel 31 that tapers or reduces in diameter in a proximal to distal direction. In one aspect, a first right-hand side wall 28 has a funnel-like shape while an opposing (second) or a left sidewall 30 has a linear shape. As a first instrument, such as instrument 16, is inserted through channel 31, the tapered channel directs instrument 16 towards left sidewall 30.

Figure 5B:
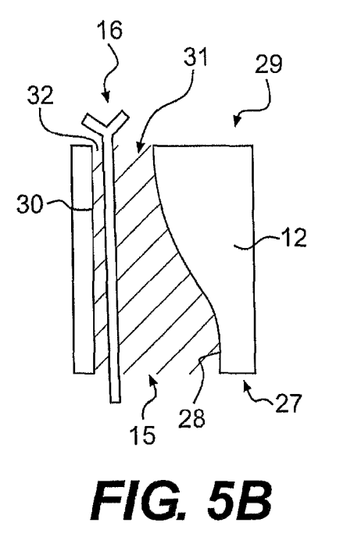
FIG. 5B is a longitudinal sectional view of the distal end of an exemplary embodiment showing a first instrument.

FIG. 5B illustrates instrument 16 inserted through channel 31 and spaced away from right sidewall 28. The shape of surface 22 can position instrument 16 closer to left sidewall 30 than to right sidewall 28.

Figure 5C:
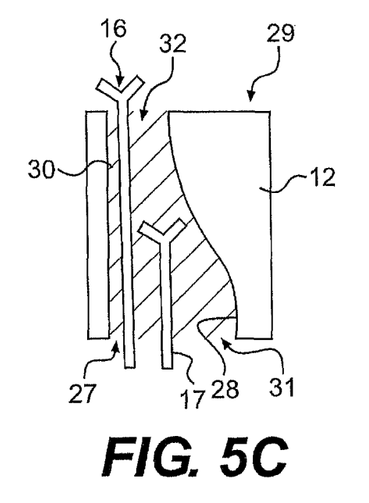
FIG. 5C is a longitudinal sectional view of the distal end of an exemplary embodiment showing a second instrument being inserted.

FIG. 5C illustrates second instrument 17 approaching surface 22. As second instrument 17 is inserted through channel 31, the position of first instrument 16 relative to sidewalls 28, 30 and the shape of surface 22 can bias second instrument 17 toward a right position with respect to first instrument 16. While funnel shaped surface 22 can initially direct instrument 16 closer to sidewall 30, subsequently inserting second instrument 17 into working channel 31 forces second instrument 17 into the space between instrument 16 and sidewall 28. As such, surface 22 operates to generally direct instruments 16, 17 to their respective locations relative to each other.

Figure 5D:
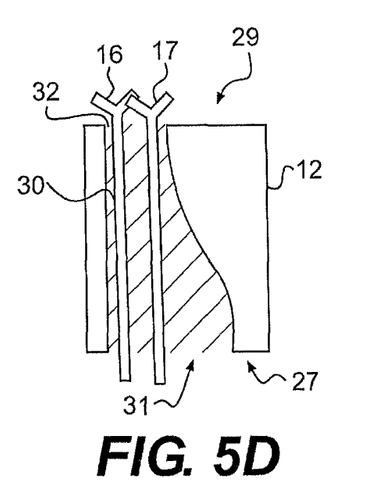
FIG. 5D is a longitudinal sectional view of the distal end of an exemplary embodiment showing a second instrument being positioned in between a first instrument and an instrument directing surface.

As instrument 17 is advanced toward distal opening 32, instrument 17 comes to generally occupy the right side of channel 31. Instrument 17 then passes between instrument 16 and sidewall 28. As illustrated in FIG. 5D, first and second instruments 16, 17 can extend beyond distal opening 32 to become located in positions relative to one another and relative to tip 12.

System 10 may not be restricted to directing the relative positioning of two instruments as surface 22 can be configured to facilitate the relative placement of more than two instruments. For example, a third instrument could subsequently be passed between second instrument 17 and sidewall 28. In another example described below with regard to FIG. 9C, an endoscope could be placed within system 10 and directed to a first position. Thereafter, first and second instruments may be inserted into system 10 and directed to two other positions, such as generally left and right, top and bottom, or other locations relative to the endoscope. In such an embodiment, one or more surfaces 22 could direct the sequential insertion of devices to select, relative locations. In another example, a first inserted device could be directed to a first position (such as a left or top position), a second inserted device could be directed to a second position (such as a center position), and a third inserted device could be directed to a third position (such as a right or bottom position).

Figure 6A:
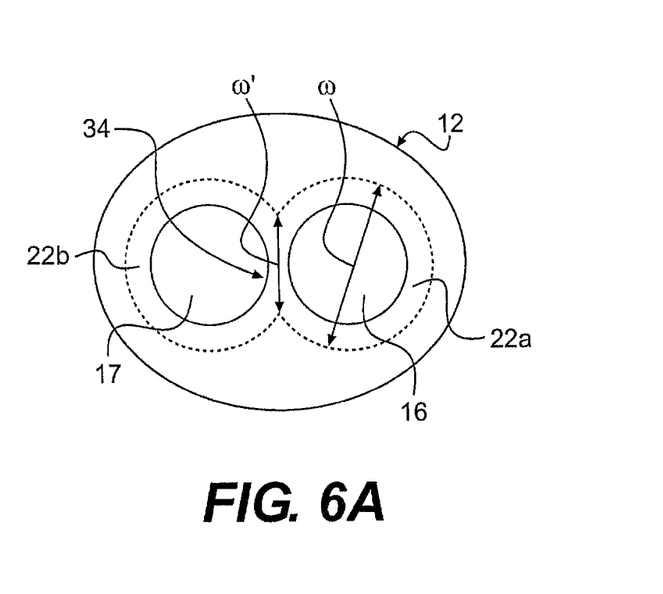
FIG. 6A is a cross-sectional view of another embodiment of a system.
Figure 6B:
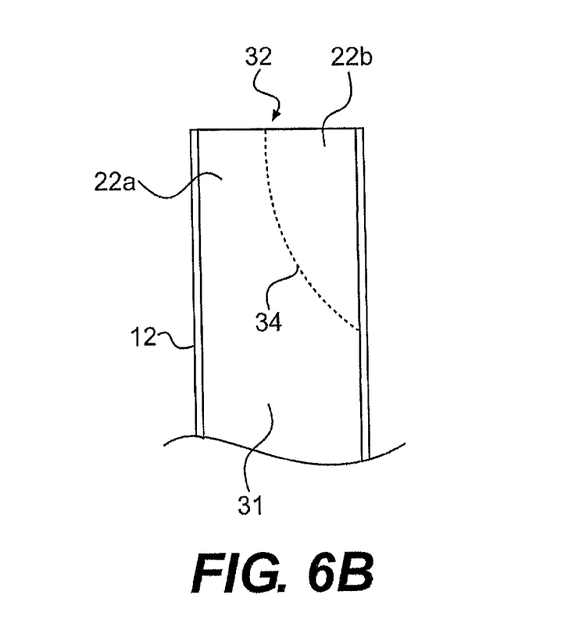
FIG. 6B is a longitudinal sectional view of the embodiment illustrated in FIG. 6A.

In another embodiment, surface 22 can include a first area 22a and a second area 22b separated by a traversable barrier 34. As shown in the FIG. 6A, first or second areas 22a, 22b may have cross-sectional widths ω and barrier 34 can have a cross-sectional width ω', where ω' can be generally smaller than the cross-sectional diameter of first instrument 16 positioned within area 22a of tip 12. Second instrument 17 can have a diameter approximately equal to or slightly smaller than the diameter of first instrument 16. As shown in FIG. 6B, barrier 34 can extend across a portion of channel 31 to selectively position a first instrument (not shown) into first area 22a. The first instrument that enters channel 31 encounters barrier 34 and barrier 34 directs this instrument to area 22a. The first instrument, as a result, occupies a select position within tip 12.

Placement of a first instrument in first area 22a can also prevent passage of a second instrument (not shown) through first area 22a. The second instrument can be forced to cross barrier 34 and occupy area 22b. Crossing barrier 34 can require some minimal amount of force such that as first instrument encounters barrier 34, the first instrument can take a path of least resistance generally around barrier 34. However once in first area 22a, the first instrument can at least partially block the path around barrier 34. If an operator subsequently inserts a second instrument into channel 31, the second instrument can be placed into area 22b after overcoming barrier 34. As such, barrier 34 can operate to selectively position a first instrument into first area 22a and selectively position a second instrument into second area 22b.

In some embodiments, barrier 34 can be formed from part of tip 12. As shown in FIG. 6A, barrier 34 can include a thin section of tip 12 residing generally between two areas within tip 12. Barrier 34 can include a polymer or metal material that may be different or similar to a material used to form tip 12. Further, barrier 34 can be at least partially formed from a flexible or a non-flexible material.

In one aspect, barrier 34 can be formed of a compressible, deformable, bendable, elastic, or resilient material. For example, upon contact with the second instrument, barrier 34 can change shape to allow passage of the second instrument into area 22b. Barrier 34 may also include a ductile or brittle material configured to rupture when a sufficient force is applied.

In another aspect, barrier 34 can be formed of a rigid or semi-rigid material. A rigid barrier 34 could include one or more spring elements configured to deflect when a force is applied. These spring elements could be surfaces which deflect when instruments are passed. Further, other spring mechanisms such as leaf or coil springs could deflect one or more instruments or be deflected by one or more instruments.

Figure 7A:
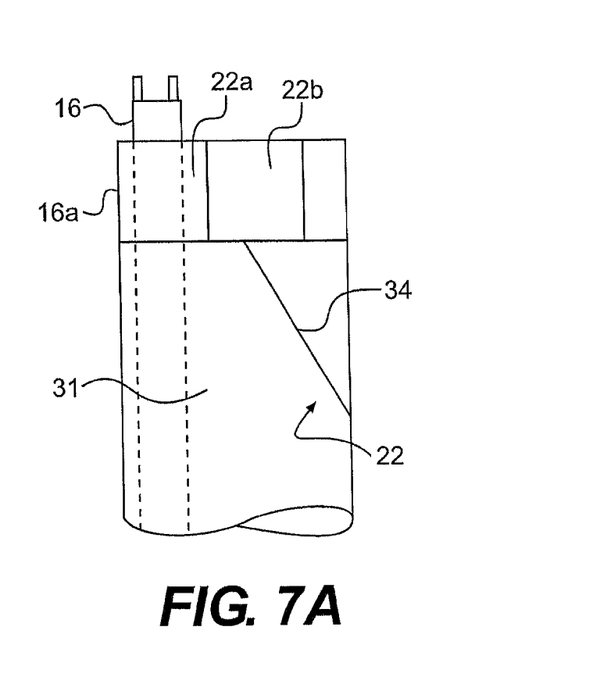
FIG. 7A is a perspective view of an exemplary embodiment showing a first instrument being guided into its select position by an instrument directing surface.

In yet another embodiment of the systems and methods described herein, barrier 34 can be a partially ramped or protruding surface feature that may partially block a section of channel 31. As shown in FIG. 7A, barrier 34 can generally prevent first instrument 16 from entering second area 22b. In addition, barrier 34 can direct the first instrument into first area 22a.

Figure 7B:
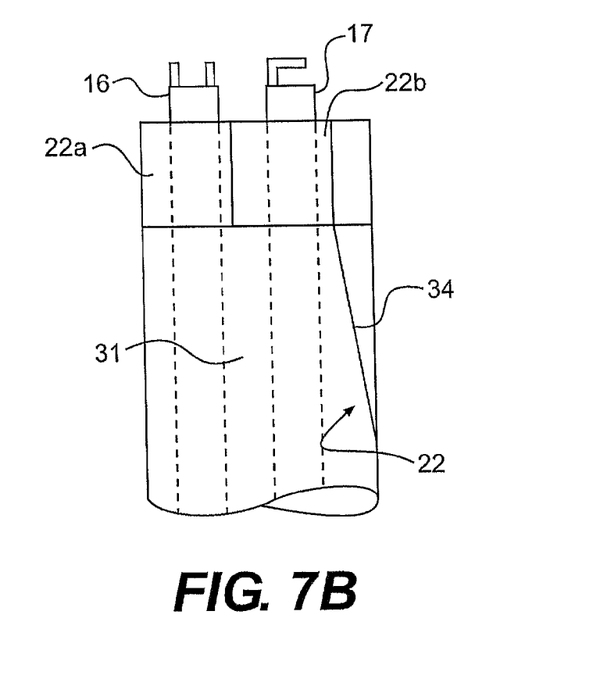
FIG. 7B is perspective view of the embodiment illustrated in FIG. 7A, showing a first instrument and a second instrument being directed into their select positions.

As shown in FIG. 7B, the ramp structure of barrier 34 can be formed of a compressible or deformable material such that second instrument 17 can compress the ramp and occupy the position in between the ramp and instrument 16. Instruments 16 and 17 can be positioned in their selective area 22a, 22b, respectively. Also, an instrument can be formed of a compressible outer sheath, such that the body of the instrument is compressed to permit passage through second area 22b.

In one aspect, surface 22 can limit movement of one or more instruments once inserted through system 10. For example, surface 22 can narrow to a dimension corresponding to the cross-sectional size and shape of instruments 16 and 17. The limited spacing between the instruments and the walls of channel 31 can inhibit relative movement of the instruments.

Figure 8A:
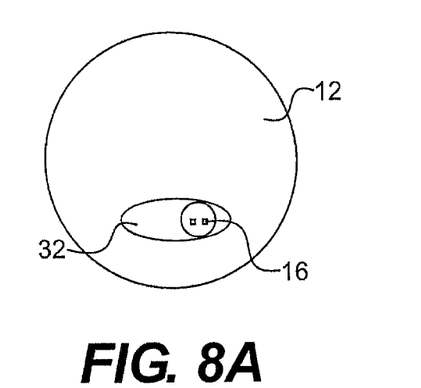
FIG. 8A is a cross-sectional view of the distal end of an exemplary embodiment.

FIG. 8A illustrates distal end 29 of tip 12, wherein instrument 16 occupies one side of opening 32. The remaining area of opening 32 has a size and shape generally corresponding to instrument 17 (not shown). Once instruments 16 and 17 are positioned within opening 32, the size and shape of opening 32 can prevent lateral movement of one or more instruments within opening 32.

Figure 8B:
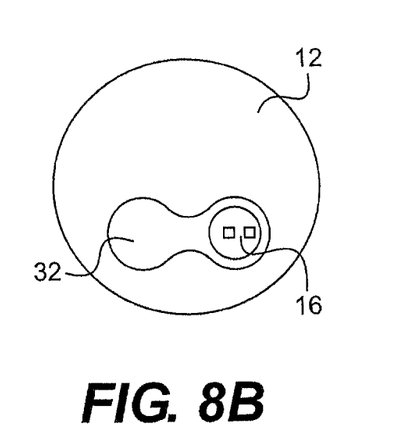
FIG. 8B is a cross-sectional view of the distal end of another exemplary embodiment.

In addition, or alternatively, the distal portion of channel 31 or opening 32 can include a dumbbell cross section or a divider that limits movement of an instrument. For example, FIG. 8B illustrates a dumbbell shaped opening 32 having a first area located beside a second area (e.g., left and right areas) configured to receive the first and second instruments. After first instrument 16 is positioned within a first, right area, the instrument can be limited from moving laterally into the second, left area.

Figure 9A:
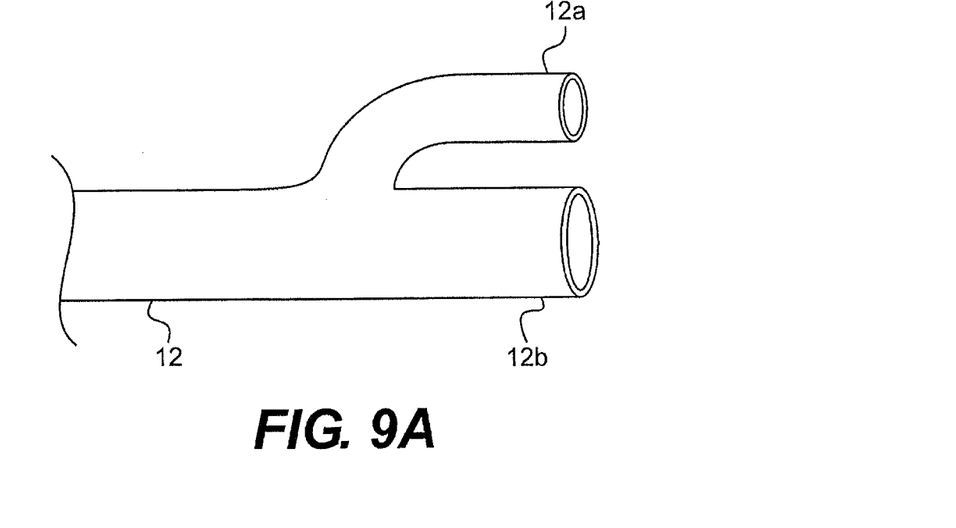
FIG. 9A is a perspective view of an exemplary embodiment wherein the working channel bifurcates into two branches.

In one aspect, surface 22 can assist with directing instruments into different branches of one or more working channels. In an exemplary embodiment, tip 12 bifurcates into multiple branches. As illustrated in FIG. 9A, tip 12 divides into branches 12a and 12b. Surface 22 can be positioned within tip 12 to selectively direct the one or more instruments inserted into tip 12 into branches 12a, 12b.

Figure 9B:
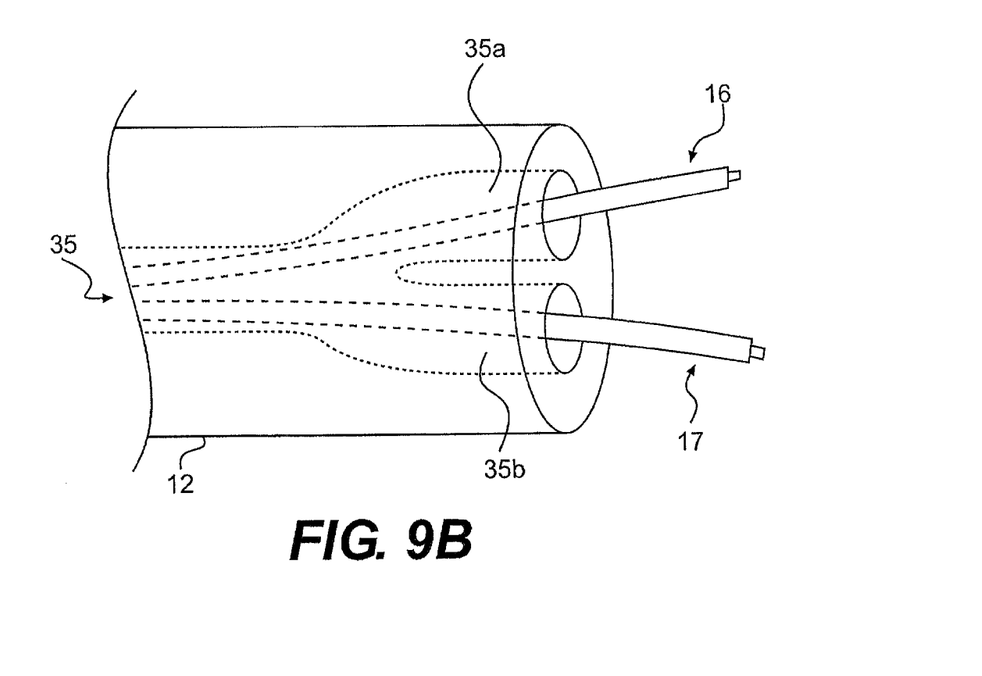
FIG. 9B is a perspective view of another exemplary embodiment wherein the working channel bifurcates into two branches showing the relative positioning of a first instrument and a second instrument.

In another embodiment, a single working channel can split into multiple channel branches. As illustrated in FIG. 9B, working channels 35a and 35b extend from a channel 35 within tip 12. As instruments 16, 17 are inserted into working channel 35, surface 22 may direct instruments 16, 17 into separate channel branches. As shown in FIG. 9B, instrument 16 can be selectively positioned in branch 35a and instrument 17 can be selectively positioned in branch 35b.

Figure 9C:
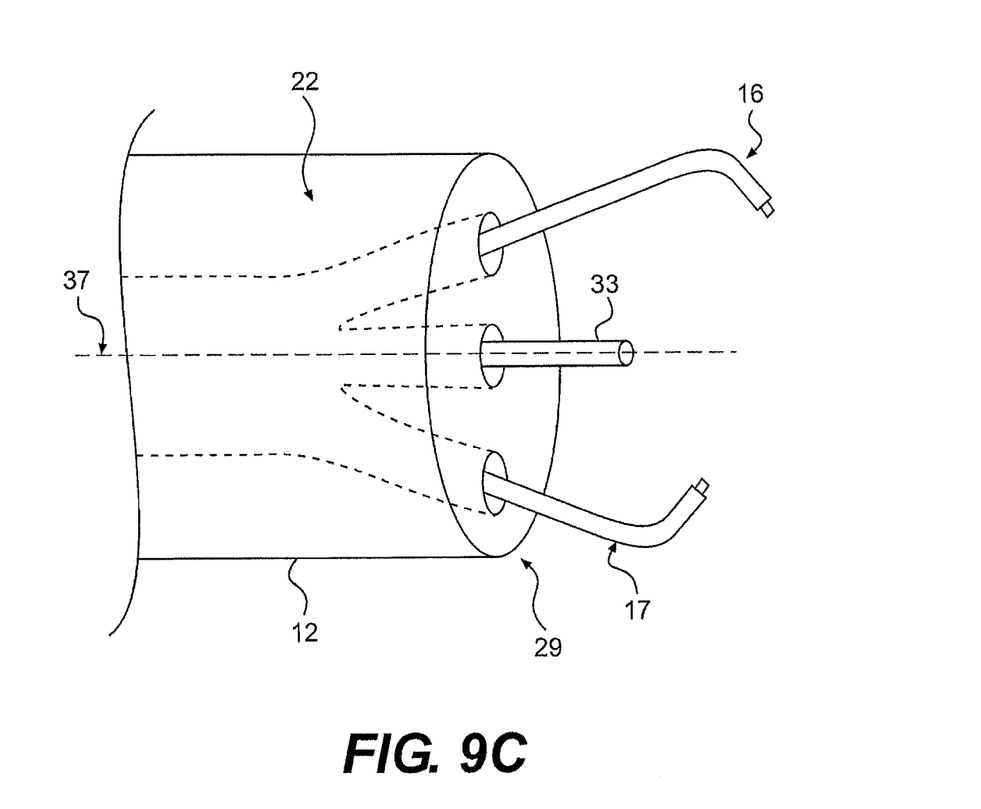
FIG. 9C is a perspective view of another exemplary embodiment wherein the working channel bifurcates into three branches showing the relative positioning of an endoscope, a first instrument, and a second instrument.

In some embodiments, multiple instruments may exit system 10 at diverging, converging, or substantially parallel angles. For example, as shown in FIG. 9C, instruments 16, 17 diverge from a longitudinal axis 37 of tip 12 and a device 33 extends generally parallel or along longitudinal axis 37. Multiple channels may differently diverge, converge, or remain parallel to axis 37. Such divergence of instruments may improve the triangulation of these instruments when used in surgical procedures.

In other embodiments, instruments 16, 17 may extend from openings along the side of tip 12, not located at the distal end of tip 12. Also, device 33 may include an endoscope, optical device or a third instrument. It is also contemplated that instruments 16, 17 and device 33 may be located in different branches or differently positioned beyond the distal end of tip 12.

In another embodiment, surface 22 or barrier 34 can be positioned within guide tube 11. For example, a lumen extending through guide tube 11 can include the various shapes and features described above with respect to tip 12. Thus, guide tube 11 can be configured with one or more surfaces 22, barriers 34, or lumens as described above for tip 12 to selectively position a plurality of instruments passed through guide tube 11. As such, an operator can insert two or more instruments through a working lumen of guide tube 11 and surface 22 within guide tube 11 can direct the one or more instruments to select locations within guide tube 11.

In yet another embodiment, system 10 can include an obturator for preventing inflow of surgical debris or biological materials through a distal opening during insertion of system 10. Exemplary obturators are disclosed in U.S. patent application Ser. No. 11/946,812, which is incorporated herein by reference. In one aspect, a dummy instrument can act as an obturator. If all of the channels are not occupied by surgical instruments, the unused channels can be blocked by dummy instruments.

An endoscopic procedure may require multiple devices to locate instruments at a surgical site. For example, depending on the size or shape of the instruments, the number of instruments, or type of procedure, a user could select an appropriate tip or guide tube from an assortment of tips and guide tubes. In one aspect, multiple guide tubes and/or tips could be packaged as a single kit and delivered to an operator. Various components may be pre-sterilized and aseptically packaged.

Embodiments of the invention also include methods of using the systems and devices described herein. In one embodiment, guide tube 11 having working channel 15 is introduced to the target site through a natural body orifice or a surgical incision. A first instrument, such as instrument 16, is then inserted into guide tube 11. Instrument 16 traverses through working channel 15 and enters tip 12, which includes inner surface 22 for directing instruments into selective positions. The shape and position of surface 22 directs instrument 16 into a first select position within tip 12 and distally of tip 12. A second instrument, such as instrument 17, is then inserted into channel tip 12 via working channel 15. The position of first instrument 16 relative to the sidewalls of tip 12 and the shape of surface 22 directs instrument 17 to the second select position within tip 12 and distally of tip 12. Thus, the first and second instruments 16, 17 are selectively positioned relative to one another and relative to tip 12 and guide tube 11. In an additional aspect, the placement of instrument 16 into the first position can limit instrument 17 from migrating into the first position.

In another embodiment, the first and second positions can correspond to first and second instrument areas 22a and 22b within inner surface 22 of working channel tip 12 or guide tube 11. Surface 22 can further include a traversable barrier 34 which limits movement of a first instrument inserted into tip 12 or guide tube 11, and can direct it away from second area 22b. As a first instrument, such as instrument 16, is inserted into a working channel, it encounters barrier 34 and is directed into area 22a. Thus, the first instrument takes a path of least resistance around barrier 34, and occupies a select position within the working channel and distal to the tip 12. As a second instrument, such as instrument 17, is subsequently inserted into channel tip 12, it encounters barrier 34 which limits its access to area 22b. When an operator moves instrument 17 into the working channel, barrier 34 can be modified, permitting instrument 17 to enter area 22b. Thus, the second instrument can be directed to a select position relative to the first instrument and relative to system 10.

In yet another embodiment, barrier 34 can change position, shape, or size to permit passage of the second instrument. In an initial configuration, barrier 34 limits one or more instruments from entering area 22b. A first instrument 16 inserted into the working channel occupies the position 22a because barrier 34 limits access of the first instrument into position 22b. When a second instrument 17 is inserted into the working channel, position 22a is occupied by the first instrument. The second instrument encounters barrier 34 which limits its access into area 22b. When an operator applies some additional force to barrier 34 by means of instrument 17, barrier 34 can change its position, shape, or size to allow passage of instrument 17 into area 22b. In one such aspect, barrier 34 is compressed or deformed by the second instrument. In another exemplary aspect, barrier 34 is pushed or slid into a new position that allows access to position 22b. Barrier 34 may also be hingedly or flexibly attached to tip 12 or guide tube 11. Thus, the first and second instruments 16, 17 are directed to select positions relative to one another and relative to the guide tube.

During a surgical procedure, the instruments can reside within system 10 until they are moved into the target site for various surgical or diagnostic applications. The instruments residing within system 10 may be introduced into the target site either simultaneously or consecutively, depending on the procedural requirements. Directing the instruments into selective positions within the working channel ensures that instruments are released at the target site in select locations relative to other instruments, optics, the guide tube, or anatomical structure.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of directing instruments to a target site of a patient, comprising:
   introducing a first instrument into a lumen of a tube, wherein the lumen is partially defined by a movable surface that is movable relative to other internal surfaces defining the lumen, the movable surface being positioned proximate to a distal end of the lumen;
   positioning a distal end of the first instrument distal to the movable surface;
   introducing a second instrument into the lumen while the first instrument is disposed in the lumen;
   causing the second instrument to contact the movable surface to move the movable surface; and
   positioning a distal end of the second instrument distal to the movable surface.

2. The method of claim 1, wherein the distal end of the first instrument extends beyond a distal end of the tube when introducing the second instrument into the lumen.

3. The method of claim 2, further comprising moving the second instrument to extend beyond the distal end of the tube.

4. The method of claim 1, wherein the tube includes a tip portion detachable from a remainder of the tube, and the tip portion includes the movable surface.

5. The method of claim 1, wherein the distal end of the second instrument is generally parallel to the distal end of the first instrument when the distal end of the second instrument is positioned distal to the movable surface.

6. The method of claim 1, wherein at least one of the first instrument or the second instrument includes an end effector, the method further comprising performing a medical procedure with the end effector.

7. The method of claim 1, wherein the movable surface is tapered such that the lumen has a cross-sectional area that is smaller at a distal portion of the lumen than at a proximal portion of the lumen.

8. The method of claim 1, further comprising causing the first instrument to contact the movable surface prior to positioning the distal end of the first instrument distal to the movable surface.

9. A method of directing instruments to a target site of a patient, comprising:
    introducing a first instrument into a proximal end of a lumen of a tube, wherein the lumen is partially defined by a movable surface that is movable relative to other internal surfaces defining the lumen, the movable surface being positioned proximate to a distal end of the lumen, and wherein the movable surface extends from a first end to a second end, the second end being distal and radially inward of the first end;
    moving a distal end of the first instrument past the movable surface;
    introducing a second instrument into the proximal end of the lumen; and
    moving the second instrument into contact with the movable surface to cause movement of the movable surface.

10. The method of claim 9, wherein the movable surface is deformable.

11. The method of claim 9, wherein the movable surface is attached to a remainder of the tube by a hinge.

12. The method of claim 9, wherein the movable surface is flexibly attached to a remainder of the tube.

13. The method of claim 9, wherein moving the distal end of the second instrument into contact with the movable surface occurs while the first instrument is disposed in the lumen.

14. The method of claim 9, wherein the movable surface changes at least one of a position, a shape, or a size upon application of force by the second instrument.

15. The method of claim 9, further comprising moving the distal end of the first instrument into contact with the movable surface.

16. The method of claim 9, wherein movement of the movable surface includes moving the second end of the movable surface radially outward.

17. A method of directing instruments to a target site of a patient, comprising:
    introducing a first instrument into a lumen of a tube, wherein the lumen is partially defined by a surface movable between a first configuration and a second configuration relative to a wall of the tube;
    moving a distal end of the first instrument past the surface;
    introducing a second instrument into the lumen; and
    moving a distal end of the second instrument into contact with the surface to cause movement of the surface from the first configuration to the second configuration.

18. The method of claim 17, wherein movement of the surface from the first configuration to the second configuration includes radially outward movement of a distal end of the surface.

19. The method of claim 17, wherein moving the distal end of the first instrument past the surface includes moving the distal end of the first instrument into contact with the surface, wherein the surface guides the first instrument into a position upon exiting the lumen.

20. The method of claim 17, further comprising positioning the distal end of the first instrument into a first position distal to a distal end of the tube, and while the distal end of the first instrument is in the first position, positioning the distal end of the second instrument in a second position distal to the distal end of the tube.

* * * * *